United States Patent [19]

Smith

[11] 3,951,145
[45] Apr. 20, 1976

[54] INTRAVENOUS MEASURING CHAMBER

[76] Inventor: Bob Lee Smith, 438 El Rancho, Santa Cruz, Calif. 95060

[22] Filed: Oct. 25, 1973

[21] Appl. No.: 409,635

[52] U.S. Cl. .................... 128/214 R; 128/214 C; 128/272; 215/247; 215/309
[51] Int. Cl.² ............................................ A61M 5/14
[58] Field of Search ........ 128/214 R, 214 C, 214 D, 128/214.2, 272, 2 F; 215/247, 248, 249, 309

[56] References Cited
UNITED STATES PATENTS

| | | | |
|---|---|---|---|
| 2,129,983 | 9/1938 | Bacon | 128/214 C |
| 2,489,600 | 11/1949 | Tydings et al. | 128/218 M |
| 2,644,452 | 7/1953 | Brown | 128/272 |
| 2,770,234 | 11/1956 | Nesset et al. | 128/214 R |
| 3,001,525 | 9/1961 | Hendricks | 128/214 C |
| 3,163,163 | 12/1964 | Wilburn | 128/272 |
| 3,216,418 | 11/1965 | Scislowicz | 128/214 C |
| 3,216,419 | 11/1965 | Scislowicz | 128/214 C |
| 3,345,980 | 10/1967 | Coanda | 128/2 F |
| 3,667,464 | 6/1972 | Alligood | 128/214 C |
| 3,776,229 | 12/1973 | McPhee | 128/214 C |

Primary Examiner—Dalton L. Truluck
Attorney, Agent, or Firm—Fleit & Jacobson

[57] ABSTRACT

An improved measuring chamber for use in an intravenous feeding set is defined by a rigid transparent plastic chamber and includes an injection site formed in a side wall of the chamber. With the injection site in this position, the tendency of dust to collect on the injection site is significantly reduced. Moreover, adding medication to the measuring chamber is easier because the attendant need not reach so high. Finally, if the injection site is located below the liquid level of parenteral fluid in the chamber, homogeneous mixing of the parenteral fluid and the medication added thereto can be accomplished by simply pumping the plunger of the hypodermic syringe used to add the medication to the chamber.

6 Claims, 4 Drawing Figures

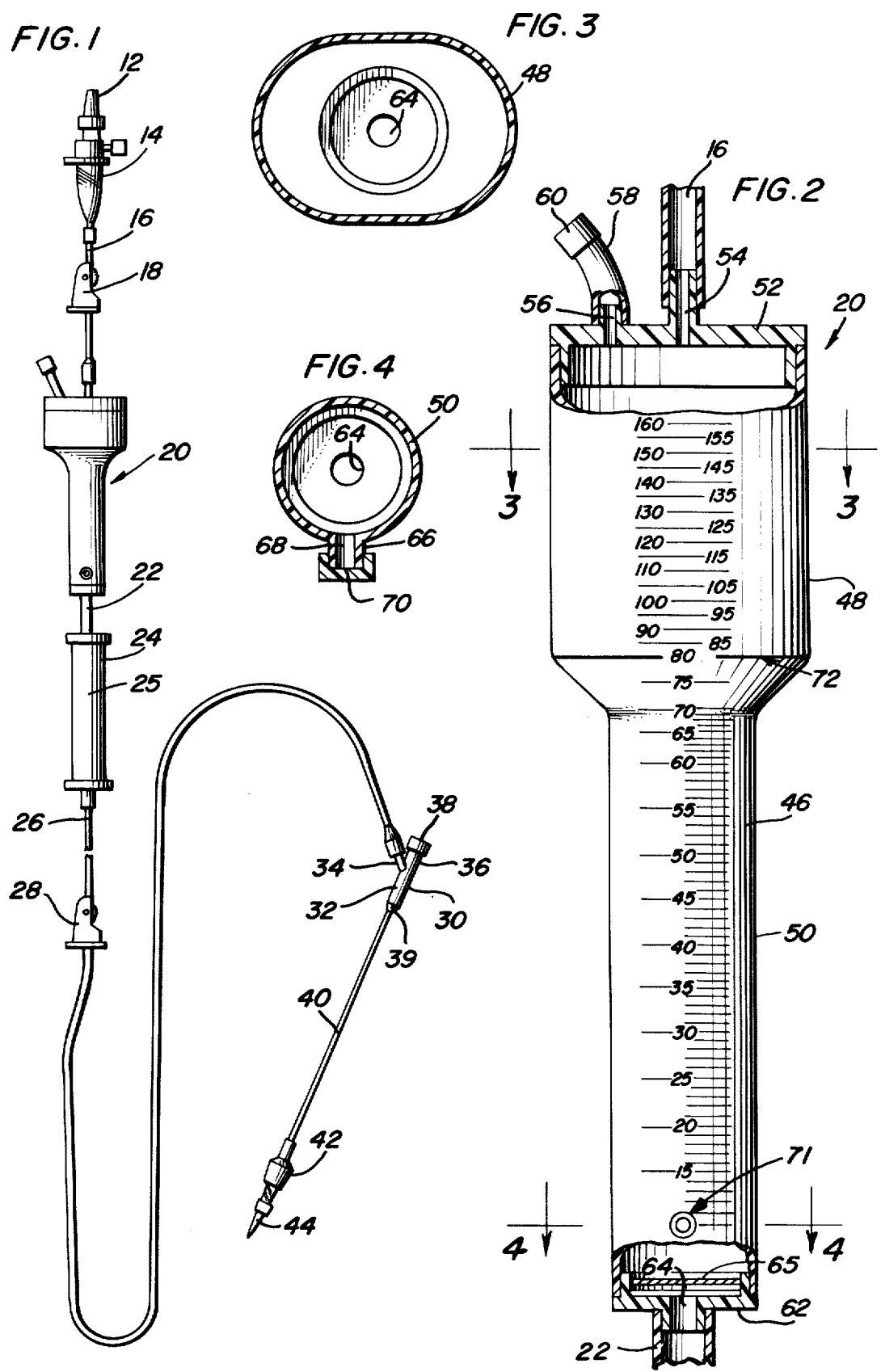

INTRAVENOUS MEASURING CHAMBER

BACKGROUND OF THE INVENTION

The present invention relates to an improved intravenous feeding set and a measuring chamber for use therein.

Conventional intravenous feeding sets for feeding a parenteral solution directly into a patient's body often include measuring chambers for precisely controlling the amount of parenteral solution fed to the patient. A typical measuring chamber takes the form of a transparent plastic chamber marked with suitable indicia in order that the amount of fluid contained therein can be determined visually. The measuring chamber is usually inserted in the flow line of the intravenous feeding set immediately downstream of the parenteral solution supply bottle, upstream of the flow control means used for controlling the parenteral fluid flow rate, and upstream of any flow rate measuring means that may be employed in the system. A second flow control clamp is usually positioned upstream of the measuring chamber for controlling the flow of parenteral fluid passing from the supply bottle to the measuring chamber.

In using an intravenous feeding set with a measuring chamber, the measuring chamber, after priming of the system, is filled with the amount of parenteral solution to be fed to the patient, this being accomplished by visual reference to the indicia on the body of the chamber. Thereafter, the flow connection between the parenteral fluid supply bottle and the measuring chamber is shut off so that no additional fluid from the supply boottle will pass into the measuring chamber. Venipuncture is then accomplished and all the fluid in the metering chamber is allowed to flow into the patient's body.

In order that specific medication can be added to the parenteral solution as it is being fed to the patient, conventional intravenous feeding sets are often provided with one or more "injection sites." Such injection sites often take the form of a plastic or rubber nipple opening directly into the flow line of the intravenous set, the nipple being covered with a rubber cap which can be pierced by a conventional hypodermic needle. Usually conventional injection sites are positioned to communicate with a flow conduit in the intravenous feeding set so that the medication can be added to a stream of parenteral fluid as it flows through the conduit. Alternately, or additionally, an injection site may be formed directly in the top of a conventional measuring chamber so that the medication can be added directly to the fluid in the measuring chamber.

Measuring chambers including injection sites formed in their tops are disadvantageous in a number of particular areas. For example, because an injection site found in the top of a measuring chamber is upward facing, it tends to collect dust when used, which is objectionable from a health standpoint. Moreover, many attendants experience difficulty in reaching an upward facing injection site formed in a measuring chamber top once the intravenous feeding set is ready for operation since the measuring chamber is usually elevated high over the patient's head during normal use.

Still another disadvantage associated with injection sites formed in the tops of measuring chambers is that they are used with difficulty when it is desirable that the medication be administered to the patient uniformly mixed in the parenteral fluid. With an upward facing injection site formed in the top of a measuring chamber, this mixing is difficult to accomplish since the medication added from the top of the chamber does not significantly mix with the parenteral fluid already in the chamber. Also, the medication may become aerated on striking the parenteral fluid surface.

Yet another disadvantage associated with injection sites formed in the tops of measuring chambers concerns removal of parenteral fluid from the chamber. To remove fluid the parenteral fluid flow must be stopped and the measuring chamber inverted. After the fluid is removed, the flow line of the intravenous set must be rebled to avoid air bubbles in the line. This procedure is not only time consuming but may result in stopping up the intravenous needle.

Accordingly, it is an object of the present invention to provide an improved measuring chamber in which the injection site associated therewith has little tendency to collect dust in use.

It is a further object of the invention to provide an improved measuring chamber including an injection site which is easy to reach when the intravenous set carrying the measuring chamber is in an operating condition.

It is a still further object of this invention to provide an improved measuring chamber which enables additional medication added to be uniformly mixed with the parenteral fluid already in the chamber so that the medication can be fed to the patient uniformly along with the parenteral fluid.

Yet another object of the invention is to provide an improved measuring chamber which enables parenteral fluid to be removed without inverting the chamber and stopping the parenteral fluid flow.

Still another object of this invention is to provide an improved measuring chamber which is of simple construction, which is easy and inexpensive to manufacture by injection molding, and which is highly accurate.

SUMMARY OF THE INVENTION

These and other objects are accomplished by the present invention in accordance with which an injection site for receiving medication to be added to a measuring chamber is directly formed in a side wall of the rigid transparent plastic member defining the body of the measuring chamber.

Because the injection site is formed in a side wall of the measuring chamber, it is laterally facing and is located vertically below the top of the measuring chamber. For this reason, this injection site is far easier to reach than an upwardly facing injection site on the top of a measuring chamber. Moreover, because the injection site is laterally facing, it is far less likely to collect dust than if it were upwardly facing. Finally, if the injection site is located in a lower portion of the measuring chamber side wall so that it is below the liquid level of parenteral fluid in the chamber, vigorous mixing of newly added medication with the parenteral fluid already in the chamber can be easily accomplished by simply pumping the plunger of the hypodermic syringe used to add the medication to the chamber before it is removed and parenteral fluid can be easily removed without inverting the measuring chamber and stopping the parenteral fluid flow.

BRIEF DESCRIPTION OF THE DRAWINGS

The present invention may be more readily understood by reference to the following drawings wherein:

FIG. 1 is a view of an intravenous feeding set constructed in accordance with the present invention and provided with the improved measuring chamber of the present invention.

FIG. 2 is a view similar to FIG. 1 showing the inventive measuring chamber in greater detail.

FIG. 3 is a cross-sectional view of the inventive measuring chamber taken on line 3—3 of FIG. 2; and FIG. 4 is a cross-sectional view of the inventive measuring chamber taken on line 4—4 of FIG. 2.

DETAILED DESCRIPTION OF THE DRAWINGS

An intravenous feeding set for feeding parenteral solution directly into a patient's body includes a piercer 12 for fluidly attaching the intravenous set to a parenteral solution supply bottle (not shown). Piercer 12 is formed from a piece of plastic material and carries a plastic chamber 14 attached thereto. Chamber 14 in turn is attached to a piece of conventional transparent flexible tubing 16, preferably made from polyvinyl chloride, which carries a conventional compression clamp 18 for controlling the flow of parenteral fluid flowing therethrough.

The lower end of flexible tubing 16 is connected as shown in FIG. 1 to the inventive measuring chamber 20. The lower portion of measuring chamber 20 is fluidly connected to a second piece of transparent flexible tubing 22, which is also preferably made from polyvinyl chloride, and which in turn is connected to a flow meter 24 such as a conventional drip chamber for enabling the operator of the intravenous set to determine the flow rate of parenteral fluid flowing through the system once at steady state.

As shown in FIG. 1, the bottom of flow meter 24 is connected to another segment of transparent flexible tubing 26, again preferably polyvinyl chloride, which also carries a flow controller 28 for controlling the flow rate of parenteral fluid passing therethrough. Any conventional compression clamp can be used as compression clamp 28, although it is preferable to employ a multi-passage flow controller of the type disclosed in commonly assigned U.S. Pat. No. 3,805,830.

Attached to the lower end of flexible tubing 26 is a conventional Y-junction injection site 30. This injection site is formed from a piece of plastic material 32 which defines an inlet conduit 34, an outlet conduit 39 and a nipple 36. As shown in FIG. 1, nipple 36 carries a rubber cap 38 thereon and is sized to receive a hypodermic needle passing through rubber cap 38.

Attached to outlet conduit 39 of Y-injection site 30 is another piece of flexible tubing 40, which again is preferably made from polyvinyl chloride. Flexible tubing 40 is in turn connected to adapter 42 which carries an intravenous needle 44 connected thereto. Any conventional adapter 42 can be used in the inventive intravenous feeding set.

Referring to FIG. 2, the details of the inventive measuring chamber will now be described. Measuring chamber 20 takes the form of a rigid transparent chamber 46, preferably made of a styrene-acrylonitrile polymer, which has an upper portion 48 and a lower portion 50. As shown in FIGS. 3 and 4, upper portion 48 of the measuring chamber has an oval cross section, while lower portion 50 has a circular cross-section. Moreover, the cross-sectional area of upper portion 48 is significantly larger then the cross-sectional area of lower portion 50.

As shown in FIG. 2, upper portion 48 of the measuring chamber is closed by end cap 52 which defines an inlet conduit 54 fluidly connected to flexible tubing 16 of the intravenous feeding set. End cap 52 also defines an access conduit 56 which is fluidly connected by means of transparent flexible tubing 58 to a semi-permeable membrane 60. Semi-permeable membrane 60 will pass air but not liquid and is provided in order to vent air which is displaced from metering chamber 20 as parenteral fluid is added thereto.

Attached to the outlet end of lower portion 50 of the measuring chamber is lower end cap 62. Lower end cap 62 defines an outlet conduit 64 therein which is fluidly connected to transparent flexible tubing 22 for passing parenteral fluid in measuring chamber 20 to flow meter 24.

Immediately above lower end cap 62 is microporous filter 65. Microporous filter 65 is permeable to liquid and is impermeable to air and is provided to prevent air bubbles in the parenteral solution from being intraveneously fed to the patient.

Referring to FIGS. 2 and 4, lower portion 50 of measuring chamber 20 near lower end cap 62 defines a nipple 66. Flow conduit 68 in nipple 66 communicates directly with the interior of lower portion 50 of the measuring chamber and is sealed by a rubber cap 70 thereon. Nipple 66 and rubber cap 70 form an injection site 71 and are provided in order that additional medication can be added directly to the parenteral fluid in the measuring chamber.

Referring again to FIG. 2, the inventive measuring chamber 20 is provided on at least one face thereof with a system of indicia generally indicated at 72. In lower portion 50 of the measuring chamber, the indicia take the form of horizontal lines spaced one above the other at distances corresponding to one milliliter intervals, every fifth line being numbered. In upper portion 48 of the measuring chamber, however, the indicia take the form of horizontal lines spaced apart by distances corresponding to 5 milliliter intervals only, each line being numerically marked. These lines and numbers in combination with the fluid level of parenteral fluid in the measuring chamber serve to indicate the volume of parenteral fluid in the measuring chamber and are used in the same way as the markings on a conventional burette are used.

In order to use the inventive intravenous feeding set, compression clamps 18 and 28 are first closed and piercer 12 inserted into a suitable parenteral fluid supply bottle. Next the parenteral fluid supply bottle is suspended and compression clamp 18 is opened until a suitable amount of parenteral fluid flows into the measuring chamber 20, for example, about 35 milliliters. Compression clamp 18 is then closed and flow meter 24 primed in a conventional manner. Compression clamp 28 is then opened and parenteral fluid in the measuring chamber is allowed to flow through the system until all air below microporous filter 65 is replaced by parenteral fluid. Thereafter, compression clamp 28 is closed and compression clamp 18 is opened so that the measuring chamber begins to fill with the desired amount of parenteral fluid, the air originally in measuring chamber 20 being vented through access conduit 56, flexible tubing 58 and semi-permeable membrane 60.

After the desired amount of parenteral fluid has filled into measuring chamber 20 as indicated by indicia 72, compression clamp 18 is closed. Intravenous needle 44 is then inserted into the patient and the system is ready to feed parenteral solution directly into the patient's body.

At this time or any time after intravenous feeding has begun, additional medication if necessary can be added to measuring chamber 20. This is accomplished by inserting the needle of a hypodermic syringe containing the desired medication into injection site 71 formed by nipple 66 and rubber cap 70 in the lower portion 50 of the measuring chamber. The plunger of the hypodermic syringe is then depressed to force the medication in the syringe into the measuring chamber. Moreover, if injection site 71 is positioned in a lower portion of the measuring chamber as shown in the illustrated embodiment so that it will be below the liquid level of parenteral fluid therein, mixing of the medication with the parenteral fluid can be easily accomplished by pumping the plunger of the syringe a number of times before it is removed from the injection site. Because of this pumping, a portion of the medication/parenteral fluid mixture in measuring chamber 20 is drawn back into and then ejected from the hypodermic syringe for each pump. This movement of the medication/parenteral fluid mixture causes significant turbulence in the mixture and hence causes the medication to be very uniformly mixed with the parenteral solution so that a homogeneous mixture of these two liquids is formed. Also, the parenteral fluid can be easily removed from the measuring chamber without inverting the chamber and stopping the parenteral fluid flow.

From the foregoing, it should be apparent that a specific and unique feature of the present invention is that this injection site is located on a side wall of the inventive measuring chamber. Because of this construction, the injection site is laterally facing and hence less likely to collect dust floating in the air than an upwardly facing injection site. Moreover, a laterally facing injection site especially when near the lower portion of the chamber makes adding a medication to the chamber far easier because the attendant need only position the hypodermic syringe horizontally and adjacent the metering chamber rather than vertically and above the chamber.

Still another advantage of the inventive measuring chamber, at least when injection site 71 is positioned below the liquid level of the parenteral fluid thereon is that complete or near complete mixing of a medication with the parenteral solution can be accomplished with relative ease and parenteral fluid can be quickly and easily removed from the chamber if desired. Such uniform mixing is very difficult to accomplish in prior art systems in which the edication is added either to injection sites communicating with flow conduits in the intravenous feeding set or to the top of a conventional measuring chamber. With the inventive intravenous set, however, mixing the medication with parenteral solution can be easily accomplished by the manner set forth above.

Finally, still another significant and unique feature of the particular inventive measuring chamber described above and illustrated in the drawings is that it can not only accommodate large amounts of fluid without being unduly long, but also accurately meter small amounts of fluid. In this regard, many conventional intravenous sets are disadvantageous in that they may be comparatively inaccurate especially when small volumes of parenteral fluid are to be fed to the patient. This problem arises because conventional measuring chambers are made to receive a significant amount of parenteral fluid, about 150-160 milliliters, for example. With measuring chambers of this capacity, one milliliter of fluid represents less than one percent of the volume of the chamber, and accordingly a one milliliter error is difficult for the operator of the measuring chamber to detect. For this reason, filling such a large measuring chamber with great precision is difficult.

Although the problem could be overcome by fashioning a measuring chamber from a long thin tube, this solution is impractical since such a tube would either be too long to be conveniently used or too small to provide the necessary capacity for use in most applications.

In order to solve this problem, the inventive measuring chamber illustrated herein has been provided with a comparatively small cross-sectional area in lower portion 50 and a larger cross-sectional area in upper portion 48. Accordingly, when a small amount of fluid is filled into the measuring chamber, it will remain in lower portion 50 of the chamber where its total volume can be exactly determined. However, when a large amount of fluid, for example 140 milliliters is filled into the chamber, it will not only occupy lower portion 50 of the chamber but also upper portion 48 where a comparatively great amount of fluid can be accommodated in a comparatively small vertical distance. Thus, the inventive measuring chamber can both accommodate large volumes of parenteral fluid in a vertically small space and still provide very accurate volumetric measurement when small amounts of parenteral fluid are to be measured.

Although only one embodiment of the present invention has been described above, it should be appreciated that many modifications can be made without departing from the spirit and scope of the invention. For example, injection site 71 formed by nipple 66 and rubber cap 70 can be located anywhere along the side of the body of the measuring chamber. Moreover, microporous filter 65 can be located in the system anywhere downstream of the measuring chamber, such as in drip chamber 24 as shown in commonly assigned U.S. application No. 291,303, filed Sept. 22, 1972, now abandoned, as well as in the base of the measuring chamber itself as above described. In addition, although measuring chamber 20 has been shown in FIG. 1 to be used in combination with a number of different elements commonly employed in intravenous feeding sets, other arrangements of conventional elements in intravenous feeding sets can be used. Further, although measuring chamber 20 illustrated above has been shown to have a discrete upper portion 48 with a large cross-sectional area and a discrete lower portion 50 with a small cross-sectional area, the specific shaping of the measuring chamber can be varied to any shape. For example, the walls defining the sides of measuring chamber 20 could form a right section of a cone. Alternatively, the side walls of chamber 20 could taper exponentially, logarithmically or in any other manner.

Finally, it should be appreciated that measuring chamber 20 need not be larger in its upper portion and smaller in its lower portion in order that the advantages of positioning the injection site on the side wall of the chamber be realized. On the contrary, these advantages will be realized regardless of the specific shape of the measuring chamber, although the capability of accurately measuring small amounts of fluid will only be realized if the lower portion of the chamber has a small cross-sectional area.

Although only a single embodiment of the present invention has been described above, it should be appreciated that many modifications can be made. All such modifications are intended to be included within the scope of the present invention, which is to be limited only by the following claims.

What is claimed is:

1. A measuring chamber for use in an intravenous feeding set comprising a rigid chamber having a top and a bottom and side walls connecting said top and bottom; said chamber having a larger cross-sectional area near its top than near its bottom with the side walls of the upper portion of said chamber being substantially vertically oriented and the side walls of said lower portion being substantially vertically oriented; an inlet fluid passageway in said top for placing said chamber in fluid communication with a source of parenteral fluid; an outlet fluid passageway in said bottom for placing said chamber in fluid communication with an intravenous needle; and indicia on said chamber extending from near said bottom to near said top for indicating the amount of fluid in said chamber; said measuring chamber further including an injection site for injecting medication into said chamber below the liquid level of parenteral fluid in said chamber, said injection site being formed in the lower portion of said side walls.

2. Apparatus according to claim 1 wherein a right cross section of said upper portion is in the form of an oval.

3. Apparatus according to claim 1 wherein a right cross section of said lower portion is in the form of a circle.

4. Apparatus according to claim 1 wherein a right cross section of said upper portion is in the form of an oval and wherein a right cross section of said lower portion is in the form of a circle.

5. Apparatus according to claim 1 wherein said lower portion carries indicia indicating the quantity of parenteral fluid therein in first intervals and further wherein said upper portion carries indicia indicating the quantity of fluid in said measuring chamber in second intervals, with said second intervals being larger than said first intervals.

6. Apparatus according to claim 1 hwerein said lower portion carries indicia indicating the quantity of parenteral fluid therein in one milliliter intervals and further wherein said upper portion carries indicia indicating the quantity of fluid in said measuring chamber in 5 milliliter intervals.

* * * * *